(12) United States Patent
Alam et al.

(10) Patent No.: US 10,379,016 B1
(45) Date of Patent: Aug. 13, 2019

(54) APPARATUS FOR INOCULATING AGAR PLATE

(71) Applicant: KING SAUD UNIVERSITY, Riyadh (SA)

(72) Inventors: Mohd Aftab Alam, Riyadh (SA); Fahad Ibrahim Al-Jenoobi, Riyadh (SA); Mohamed Hamed M. Al-Agamy, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/134,915

(22) Filed: Sep. 18, 2018

(51) Int. Cl.
| | |
|---|---|
| *C12M 1/24* | (2006.01) |
| *C12M 1/26* | (2006.01) |
| *C12M 3/00* | (2006.01) |
| *G01N 1/30* | (2006.01) |
| *G01N 1/31* | (2006.01) |

(52) U.S. Cl.
CPC .............. *G01N 1/31* (2013.01); *C12M 23/08* (2013.01); *C12M 23/54* (2013.01); *C12M 33/00* (2013.01); *G01N 1/30* (2013.01); *G01N 2001/317* (2013.01)

(58) Field of Classification Search
CPC ...... G01N 1/31; G01N 1/30; G01N 2001/317; C12M 23/08; C12M 23/54; C12M 33/00
See application file for complete search history.

(56) References Cited

U.S. PATENT DOCUMENTS

| | | | | |
|---|---|---|---|---|
| 6,277,642 | B1 * | 8/2001 | Mentzen et al. | G01N 35/00 436/174 |
| 7,682,821 | B2 * | 3/2010 | Woods et al. | C12M 21/02 126/569 |
| 2002/0179848 | A1 * | 12/2002 | Feygin | B01L 3/0268 250/458.1 |
| 2014/0099679 | A1 | 4/2014 | Banks | |

FOREIGN PATENT DOCUMENTS

| | | | | |
|---|---|---|---|---|
| CN | 2673078 Y | | 1/2005 | |
| CN | 107022476 A | | 8/2017 | |
| DE | 196 31 977 | * | 1/2001 | ............ C12M 23/10 |
| DE | 19631997 C2 | | 4/2001 | |
| KR | 101389628 B1 | | 5/2014 | |
| WO | WO 99/63324 | * | 12/1999 | ............... G01N 1/30 |

OTHER PUBLICATIONS

Kawaguchi et al., "New method for isolating antibiotic-producing fungi", The Journal of Antibiotics (2013), vol. 66, pp. 17-21.
Litzlbauer et al., "Large Scale Bacterial Colony Screening of Diversified FRET Biosensors", PLOS ONE (2015)17 pages.

* cited by examiner

*Primary Examiner* — Gautam Prakash
(74) *Attorney, Agent, or Firm* — Richard C. Litman

(57) ABSTRACT

The apparatus for inoculating agar plates includes a spray chamber having an upper opening for receiving an atomized microbial suspension and a lower opening for receiving an agar plate. The apparatus also includes an atomizer including a reservoir and a fluid tube for delivering the microbial suspension to the atomizer nozzle. A containment feature extends around an inner surface of the spray chamber to catch any drop that may form on its inner wall and advance down towards the lower opening. The spray chamber allows multiple agar plates to be quickly inoculated without cross-contamination of agar habitats, without contaminating the outside of the plates, and without contaminating the work area.

5 Claims, 3 Drawing Sheets

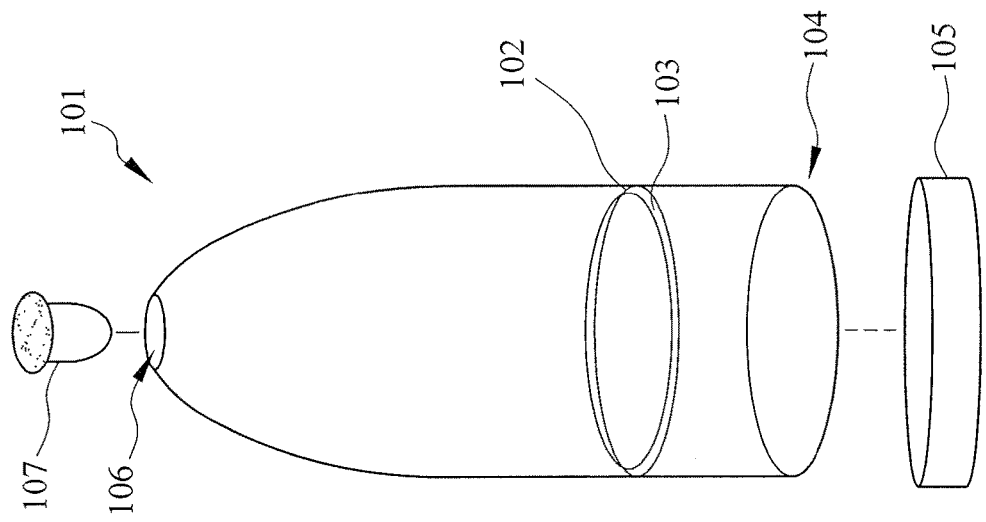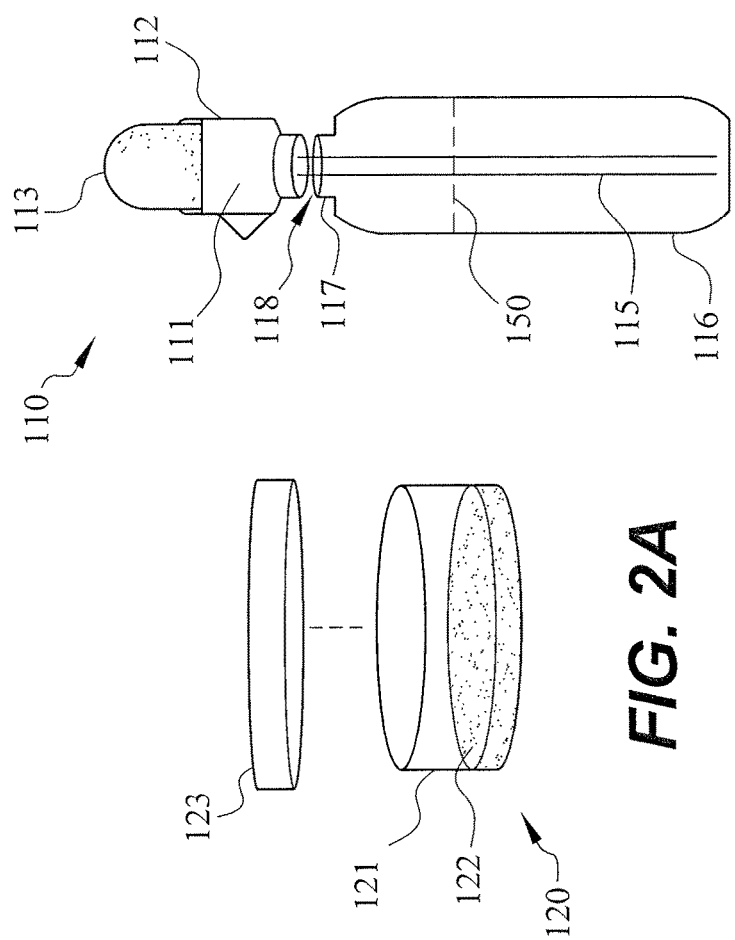

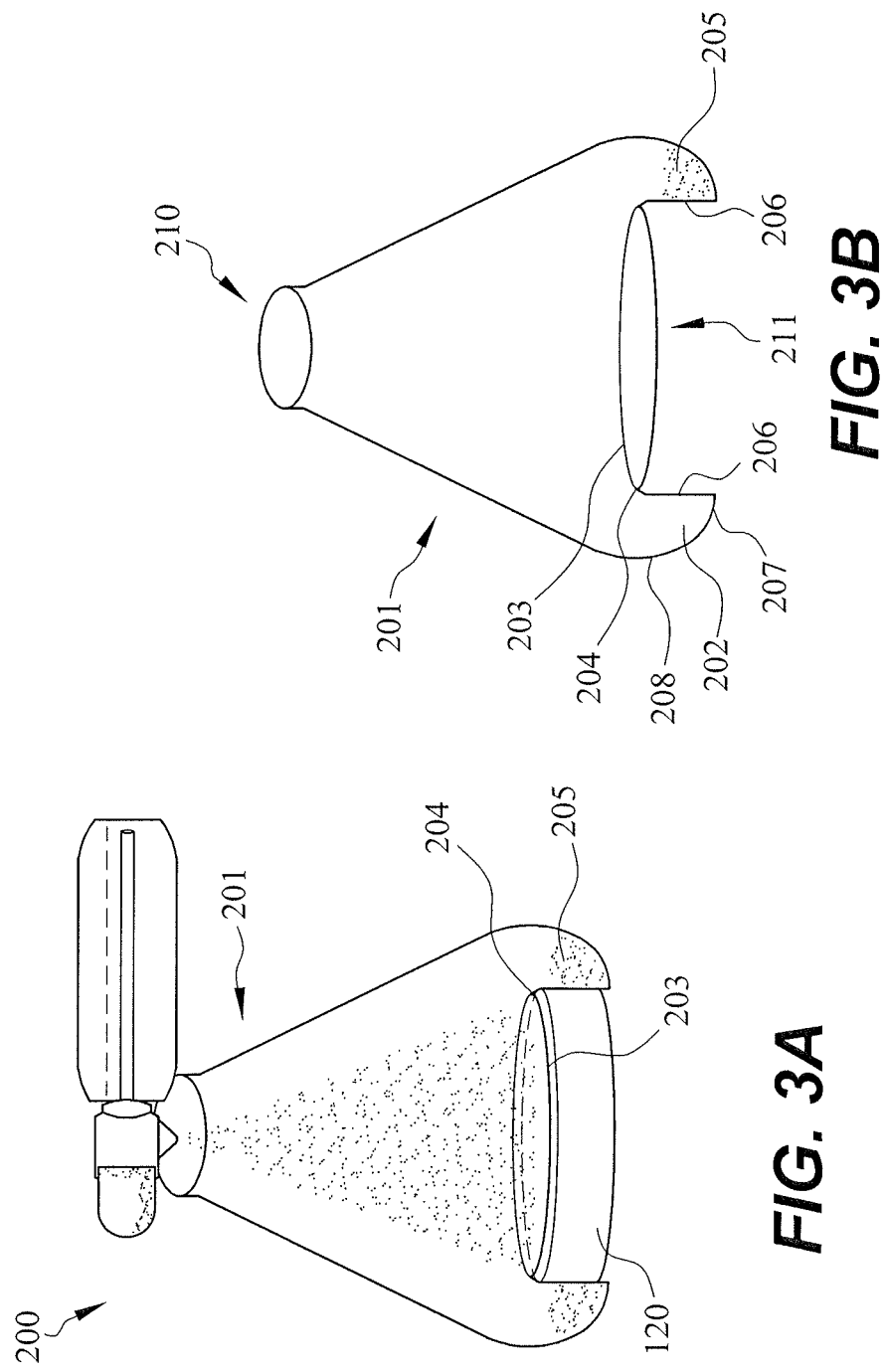

APPARATUS FOR INOCULATING AGAR PLATE

BACKGROUND

1. Field

The disclosure of the present patent application relates to microbial culturing, and particularly to an apparatus for inoculating agar plates with microorganisms.

2. Description of the Related Art

In microbiology, agar plates are used for several purposes, for example: disease diagnosis, susceptibility testing, estimating concentration of microorganisms in a sample, to isolate pure colonies, screening experiments, microbial detection and identification. To prepare an agar plate, the molten agar medium is poured into an agar plate and solidified by cooling. A microbial suspension is applied on the surface of agar media using different techniques. Some examples of these techniques include streak plating, spread plating, pour plating, and soft agar overlays. In streak and spread plating techniques, the microbial inoculum is transferred onto the agar plate and then spread over the surface of the media manually using an inoculator (a wire loop or glass loop or disposable plastic loop, for streaking) or a spreader (an L-shaped glass or metal rod, or cotton swab, or pre-sterilized glass beads, for spreading the microbes). While spreading or streaking the microbial inoculum on agar surface, problems with uneven spreading and discontinuous streaking of the microbes may lead to failed experiments and waste of time, as well as material. Another problem caused by wire loop, glass spreader, or cotton swab application is damaging the surface of the solidified agar media, which may occur when manually streaking or spreading the culture media. Sometimes, it is also observed that the culture did not reach the inner peripheral areas of the agar plate when using the L-shaped spreader. If microbial inoculum is absorbed in the center of the plate, it leads to condensed colonies in the center of the plate, which cannot be distinguished properly. The manual inoculation of agar plates by spreading or streaking technique is a slow process and requires a lot of attention and care to avoid damage to the agar surface. Accordingly, both manual spreading and streaking are time-consuming techniques.

Thus, an apparatus for inoculating agar plates solving the aforementioned problems is desired.

SUMMARY

The apparatus for inoculating agar plates includes a spray chamber having an upper opening for receiving an atomized microbial suspension and a lower opening for receiving an agar plate. The apparatus also includes an atomizer including a reservoir and a fluid tube for delivering the microbial suspension to the atomizer nozzle. A containment feature extends around an inner surface of the spray chamber to catch any drops that may form on its inner wall and advance down towards the lower opening. The spray chamber allows multiple agar plates to be quickly inoculated without cross-contamination of agar habitats, without contaminating the outside of the plates, and without contaminating the work area.

The apparatus is used by positioning an agar plate within the lower opening of the spray chamber. The atomizer is secured to the top of the spray chamber so that an atomized microbial suspension may be sprayed through the upper opening of the spray chamber and onto the agar. Any drops that form on the inner surface of the spray chamber are caught by the containment feature.

These and other features of the present disclosure will become readily apparent upon further review of the following specification and drawings.

BRIEF DESCRIPTION OF THE DRAWINGS

FIG. 2A is a perspective view of an agar plate and cover for use with the apparatus for inoculating agar plates of FIG. 1.

FIG. 2B is a front view of the atomizer component of the apparatus of FIG. 1.

FIG. 2C is a perspective view of the spray chamber component of the apparatus of FIG. 1.

FIG. 3A is an environmental perspective view of an alternative embodiment of an apparatus for inoculating agar plates.

FIG. 3B is a perspective view of the spray chamber of the apparatus of FIG. 3A.

Similar reference characters denote corresponding features consistently throughout the attached drawings.

DETAILED DESCRIPTION OF THE PREFERRED EMBODIMENTS

Figure 1:
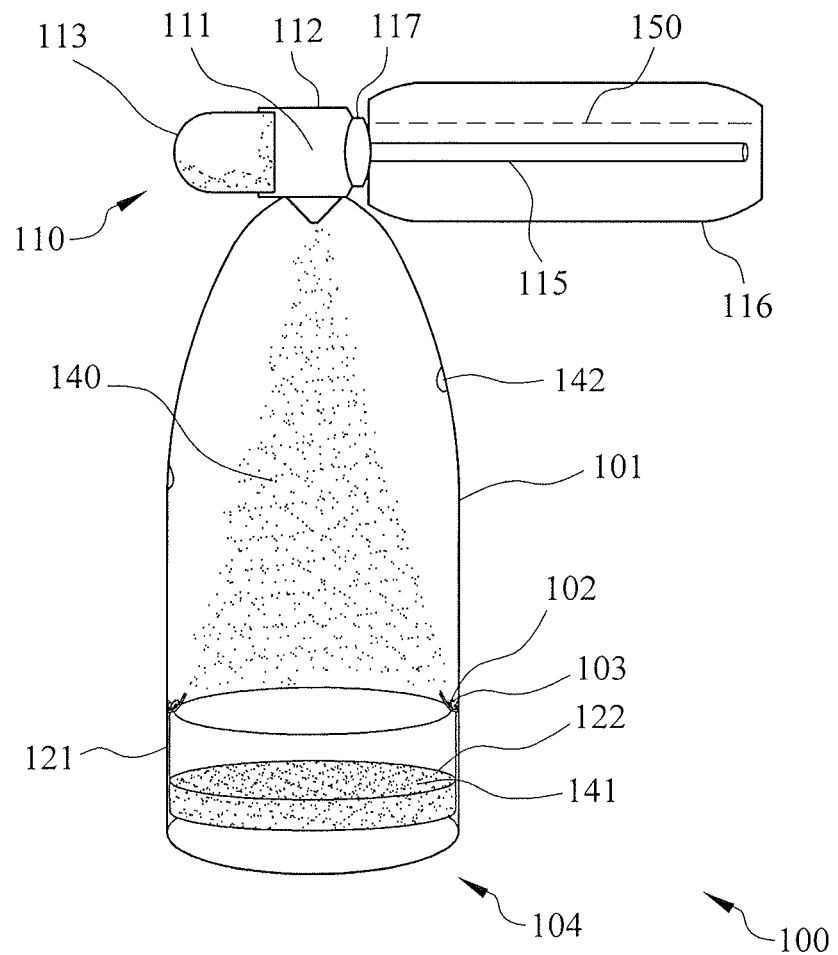
FIG. 1 is an environmental perspective view of an apparatus for inoculating agar plates.

The apparatus for inoculating agar plates includes a spray chamber having an upper opening for receiving an atomized microbial suspension and a lower opening for receiving an agar plate. The apparatus also includes an atomizer including a reservoir and a fluid tube for delivering the microbial suspension to the atomizer nozzle. A containment feature extends around an inner surface of the spray chamber to catch any drops that may form on its inner wall and advance down towards the lower opening. The spray chamber allows multiple agar plates to be quickly inoculated without cross-contamination of agar habitats, without contaminating the outside of the plates, and without contaminating the work area.

A first embodiment of an apparatus and method for inoculating agar plates is shown in FIG. 1. The apparatus 100 includes a spray chamber 101, and an atomizer 110 having a fluid tube 115 and a reservoir 116. The spray chamber 101 has one upper narrow opening 106 and a lower wide opening 104. The lower wide opening 104 is located at the base of the spray chamber 101, while the upper narrow opening 106 is located at the top of the chamber 101. The microbial suspension is sprayed through the upper opening 106 of the spray chamber 101. The lower opening 104 of the spray chamber 101 is designed in such a way that it holds the whole agar plate 120 inside the spray chamber 101. The outer vertical wall 121 of the agar plate 120 intimately contacts the inner wall of the spray chamber 101. The resultant system creates a closed environment between the atomizer and agar plate.

An annular "J" shaped inner projection 102 or lip is located on the inner surface of spray chamber 101 close to lower opening 104. The projection 102 extends around the entire periphery of the inner wall resulting in a seamless barrier. The level of inner projection 102 on the inner surface of spray chamber 101 is such that the inner projection 102 is just above the vertical wall 121 of agar plate 120 (a petri dish with agar media contained therein), or just touches the top of the vertical wall 121 of the agar plate 120. Close proximity between the top of the agar plate wall 121 and the projection 102 does not allow atomized microbes to reach the wall of the spray chamber 101 below the projection 102. The projection 102 is slightly obliquely upward, as presented in FIG. 1. A "J" shaped projection was chosen because spray droplets will either be caught by the projection or land on the inner surface of the agar plate wall. The area below the projection is intended to stay clean so that future agar plates can be inoculated without being cross-contaminated.

The inner projection 102 may include a layer of absorbent or adsorbent material 103 on its upper surface. While the microbial suspension is sprayed over the agar surface 122, some of the spray droplets may fall on the inner wall of the spray chamber 101 above the projection 102. When a large number of agar plates are inoculated, the small droplets on the inner wall of the spray chamber 101 will form large drops 142. After attaining the sufficient size or weight, the drops 142 will descend or roll down the inner wall of the spray chamber 101 towards the agar plate 120, as depicted in FIG. 1 at 141. The primary function of inner projection 102 and the absorbent circular strip 103 is to absorb and stop the drops descending down the inner wall of the spray chamber before they drip into the agar of the agar plate 120, potentially cross-contaminating the specimen. The inner projection 102 is also intended to prevent drops 142 from falling onto the work area and prevent spray droplets 140 from contaminating the outer side of the side wall 121 of agar plate 120. The position and dimensions of the inner projection 102 are arranged in such a way that it can cover the plate wall 121 from the falling atomized particles 140 and the drops 142, but allows the inoculation of a maximum area of the agar surface 122.

While the apparatus 100 is not in use, the lower opening 104 and upper opening 106 of the spray chamber 101 may be sealed with the covers or closure elements 105 and 107, respectively.

FIG. 2A details the agar plate 120. As seen in FIG. 2A, the agar plate 120 is shaped as a cylinder having a closed bottom and an open top. The walls 121 are dimensioned and configured to match or fit closely inside the inner surface of the spray chamber 101 for creating the necessary intimate contact that will prevent the atomized spay 140 from exiting the enclosure through a gap between the agar plate wall 121 and the chamber 101. The level of the projection member 102 in the spray chamber 101 is kept according to the height of the wall 121 of the agar plate 120. The upper rim of the wall 121 should rest immediately adjacent to the projection 102 when the apparatus is set up for inoculation.

Any agar media known in the art for culturing microorganisms is contemplated with the apparatus, while Mueller-Hinton Agar is preferred. Other types of agar may include Tryptic Soy Agar, Chocolate Agar, Thayer-Martin Agar, MacConey Agar, Eosin-methylene Blue Agar, Hektoen Agar, Mannitol Salt agar, and Sheep Blood Agar. Specific agars can be selected based on the type of bacteria being cultivated and the purpose of the cultivation.

The microbial suspension for inoculation is filled in the reservoir 116 of the atomizer 110, shown in FIG. 2B. The atomizer 110 has a body 112 that encases the atomizer components 111. An actuator knob 113 is provided to activate the atomizer components. The reservoir 116 has a narrow neck 117 and an opening 118 in the neck through which the fluid tube 115 passes into the actuator assembly. The body 112 of the actuator 110 is fixed over the neck 117 of the reservoir 116. All the components of the apparatus are sterilizable.

The atomizer 110 includes an atomizer nozzle, and through the application of pressure and gas, transforms the liquid stream into many small droplets. Preferably, the atomizer 110 is designed to produce a conical spray stream that creates a circular spray pattern. A fluid tube 115 is attached to the inlet of the atomizer 111 for drawing liquid from the bottom of the reservoir 116. It is contemplated that the fluid tube 115 be curved towards the direction of the bottom of the reservoir 116 so it can draw maximum fluid, indicated by dash lines 150 in FIGS. 1 and 2B, from the reservoir 116 when the atomizer 110 is in the horizontal spraying position seen in FIG. 1.

FIG. 2C details the spray chamber 101 and its components. As seen from FIGS. 1 and 2C, the chamber 101 gradually tapers out from the narrow opening 106 to the wide opening 104 creating an enclosure with a parabolic or hyperbolic shape. In a preferred embodiment the chamber 101 is transparent. A transparent chamber 101 will allow a user to confirm the items within the chamber 101 are properly positioned, and also confirm that the atomizer 110 and "J" shaped projection 102 are performing their intended functions. The "J" shaped inner projection 102 is shown in the lower portion of the chamber 101. The absorbing material within the channel of the "J" shaped inner projection 102 may be any inexpensive, replaceable material, such as cotton, polymer foam, or absorbent paper or sponge. Preferably the material is removable, thus allowing a user to remove the contaminated absorbent strip before the device is disinfected. Once the device is disinfected, a new strip can be placed in the channel. The upper closure element 107 and the lower closure element 105 may be used to seal the spray chamber 101 when not in use. Sealing the chamber 101 will prevent the surrounding work space from being contaminated by the microbes in the spray chamber 101 and will also prevent the spray chamber 101 from being contaminated from microbes in the surrounding area.

FIGS. 3A and 3B shows a second embodiment of present invention. The apparatus 200 comprises an atomizer 110 and a spray chamber 201. The spray chamber 201 has an upper narrow opening 210 and a lower wide opening 211. The agar plate 120 is placed in the lower wide opening 211. The spray chamber 201 has an elevated circular wall 206 extending up from its base 207. The lower wide opening 211 is formed at the top of the elevated circular wall 206. The peripheral bottom forms the base 207 of the chamber 201. An annular cavity 202 is formed between the elevated circular wall 206 and the outer wall 208 of the chamber 201. The annular cavity 202 will receive descending drops 142 coming from the inner side walls of the chamber 201 and prevent contamination of the agar plate 120. Optionally, an absorbent material 205 can be placed in the annular cavity 202 to absorb the extra spray droplets falling outside the surface area of agar plate 120 and the drops 142 descending down the side walls of the chamber 201. The position of the lower wide opening 211 is slightly tapered 204 from the top of the elevated circular wall 206 towards the center. The diameter of circular brim 203 of lower opening 211 is slightly smaller than the inner diameter of petri plate 120. The tapering 204 is adjusted in such a way that it will cover the side wall 121 of the agar plate 120 from direct contact with microbial spray, but allows maximum inoculation of the agar surface. While the apparatus is not in use, the lower as well as upper opening of the chamber 201 can be closed with suitable caps.

The apparatus for inoculating agar plates quickly and uniformly inoculates the microorganism on the surface of agar plate. Almost the entire surface of the agar is inoculated. The apparatus was tested for microbe growth on an agar plate after a single actuation of the atomizer and after double actuation of the atomizer. Double actuation produces more dense and uniform microbial growth. However, the microbial growth from a single actuation may be suitable in many cases. Additionally, inoculation was completed successfully without causing any damage to the surface of solidified agar media.

The number of colonies grown on the surface of agar plate will depend on the density of inoculum (number of CFU/ml) and the numbers of actuations applied, and the volume delivered by the actuator. If the density of inoculum (number of CFU/ml) is low ($1\text{-}2\times10^3$ to $1\text{-}2\times10^5$ CFU/mL), then a higher number of actuations is required to provide uniformly dense growth over the agar plate, but if the density of inoculum is higher ($1\text{-}2\times10^5$ CFU/mL), then single or double actuation may be sufficient to achieve the required dense and uniform growth on the surface of the plate.

The density and uniformity of microbial growth on the plate surface will be influenced by: number of colony forming units in the inoculum, number of atomization sprays, volume of inoculum delivered by the atomizer per atomization, the atomization efficiency of the atomizer, the distance between the nozzle of the atomizer and the agar surface, and angle of atomization. One can optimize the number of actuations required based on these parameters.

A method for inoculating an agar plate includes positioning an agar plate 120 within the lower opening of a spray chamber 101, having a ridge 102, and an absorbing material 103, as seen in FIG. 1. Optionally size of the atomized droplets, angle of the atomized spray stream, angle of atomization, the distance between the nozzle of the atomizer and the agar surface and microbial density in the microbial suspension may be adjusted. The method includes spraying an atomized microbial suspension through the upper opening 106 of the spray chamber 101 and onto the agar 122; and removing the agar plate 120 without any microbial suspension leaking out of the spray chamber by use of cover 123 as seen in FIG. 2A. The method may further include repeating the process on multiple agar plates without cross-contaminating the agar habitats, without contaminating the outside of the agar plates, and without contaminating the work area. The opening of the spray chamber may be sealed with coverings when the chamber is not in use.

In an experiment, Mueller-Hinton Agar plates were prepared. Forty grams of Mueller-Hinton Agar (MHA) was suspended in 1 liter distilled water and then boiled to dissolve the powder completely. The medium was sterilized by autoclaving at 121° C. for 15 min. After autoclaving, the medium was cooled to 45° C. and poured 25 mL molten agar into sterile 90 mm diameter Petri dishes (petri plates) to give a depth of about 4 mm. The surface of the agar was dried to remove excess moisture before use.

The inoculum (microbial suspension) of *S. aureus* strain ATCC 2913 was prepared by selecting three to five morphologically similar colonies from overnight growth (16-24 h of incubation) on blood agar medium with a sterile loop and suspending the colonies in sterile normal saline to the density of a McFarland 0.5 standard, approximately equivalent to $1\text{-}2\times10^8$ CFU/mL. The suspension density was measured by using an UV spectrophotometer. The density of the suspension was adjusted to McFarland 0.5 by addition of saline or more organisms. The number of colony forming units (CFU/ml) in the culture samples plays an important role in the incubation of the agar plates. For colony isolation, diluted microbial suspension (about $1\text{-}2\times10^3$ CFU/ml) can be sprayed over agar plate.

For comparison, some agar plates were inoculated by cotton swab. A sterile cotton swab was dipped into the bacterial suspension ($1\text{-}2\times10^8$ CFU/ml) and the excess fluid removed by turning the swab against the inside of the tube to avoid over-inoculation of plates. The inoculum was spread evenly over the entire surface of the agar plate by swabbing in three directions.

Other agar plates were inoculated by using the present apparatus. The agar plates were inoculated with inoculum of bacterial suspension ($1\text{-}2\times10^8$ CFU/ml). The bacterial suspension was filled in the reservoir of the present apparatus and then sprayed uniformly using the atomizer over an agar plate held inside the spray chamber using the atomizer.

Antimicrobial susceptibility tests of the *S. aureus* strain ATCC 29213 was determined by the disc diffusion method according to the recommendations and guidelines of Clinical Laboratory Standard Institutes (CLSI M100-S24; 2014). A panel of commercial antibiotic discs comprising Gentamicin (GM), Amikacin (AN), Chloramphenicol (C), Imipenem (IPM), Tetracycline (TE), Cefepime (FEP), Sulfamethoxazole/trimethoprim (SXT), Aztreonam (ATM) was used for susceptibility testing. All commercial antibiotic discs were purchased from BBL (Becton Dickinson, USA).

The predetermined panel of antimicrobial disks was applied firmly on the surface of inoculated Mueller-Hinton agar media by using a disc dispenser device.

Within 15 min of application of antimicrobial disks, the plates were inverted and incubated aerobically at 35-37° C. for 18-20 h.

After incubation, inhibition zones were read at the point where no obvious growth is detected by the unaided eye when the plate was held about 30 cm from the eye. The inhibition zone diameters were measured to the nearest millimeter with a ruler. The plates were read from the back of the plate with reflected light against a dark background. Zone diameters of antibiotics in swab inoculated plate were compared with zone diameter in apparatus-inoculated plates. The results of zone diameters are presented in table 1.

TABLE 1

Testing for zone of inhibition (mm)

| Antibiotic Disc | Apparatus:- Single actuation | Method of Inoculation Apparatus:- Double actuation | Swabbing |
|---|---|---|---|
| AN | 26 | 23 | 22 |
| SXT | NZI | NZI | NZI |
| TE | 25 | 24 | 22 |
| C | 22 | 22 | 21 |
| GM | 22 | 22 | 21 |
| IPM | 38 | 38 | 38 |
| ATM | NZI | NZI | NZI |
| FEP | NZI | NZI | NZI |

NZI—No zone of inhibition
Microbial concentration = $1\times10^8$ CFU/ml

As indicated by Table 1, the spray inoculation created similar results to the swabbing technique. The differences in results are minor, especially when comparing the double-actuated results. Differences of 1-2 mm are normal for separate zones of inhibition and are not indicative of substantial differences in antimicrobial activities. Therefore, when properly optimized, the spray technique discussed above will produce equivalent results to currently known techniques, such as swabbing, in a fraction of the time.

It is to be understood that the apparatus for inoculating agar plates is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. An apparatus for inoculating agar plates, comprising:
    a spray chamber defining a one piece continuous enclosure having an upper opening and an opposite lower opening, the lower opening being dimensioned and configured to receive and closely fit around the agar plate;
    a collector extending around the entire periphery of the interior wall of the spray chamber adjacent the lower opening and providing a seamless barrier for liquid drops descending down the spray chamber, wherein the collector comprises an upwardly angled projection; and
    an atomizer mounted on top of the spray chamber, the atomizer having an atomizer nozzle, a fluid reservoir extending below the nozzle, an actuator, and a fluid delivery tube extending from the actuator into the fluid reservoir, the atomizer being aligned with the upper opening in the spray chamber to direct a spray towards the lower opening when the actuator is actuated.

2. The apparatus for inoculating agar plates according to claim 1, further comprising an absorbent material disposed on an upper surface of the projection.

3. The apparatus for inoculating agar plates according to claim 1, wherein the projection is "J" shaped.

4. The apparatus for inoculating agar plates according to claim 3, wherein the atomizer nozzle produces a spray when actuated having a conical shape, the spray having an outer edge aligned to contact a circumference of the inner surface of the spray chamber between the projection and lower opening.

5. A method for inoculating an agar plate, comprising the steps of:
    filling the reservoir of the atomizer of the apparatus of claim 1 with a microbial suspension;
    positioning the agar plate within the lower opening of the spray chamber;
    mounting the atomizer on top of the spray chamber with the atomizer nozzle aligned with the upper opening in the spray chamber; and
    actuating the actuator of the atomizer in order to spray the microbial suspension onto the agar plate.

* * * * *